(12) United States Patent
Kitamura et al.

(10) Patent No.: US 6,428,812 B1
(45) Date of Patent: Aug. 6, 2002

(54) PROCESS FOR PRODUCING GRANULES CONTAINING ANGIOTENSIN-CONVERTING ENZYME INHIBITING PEPTIDES

(75) Inventors: Shuji Kitamura, Tokyo; Takashi Ueyama, Kanagawa-ken, both of (JP)

(73) Assignee: Calpis Co., Ltd., Tokyo (JP)

( * ) Notice: Subject to any disclaimer, the term of this patent is extended or adjusted under 35 U.S.C. 154(b) by 0 days.

(21) Appl. No.: 09/231,449

(22) Filed: Jan. 14, 1999

(30) Foreign Application Priority Data

Jan. 11, 1999 (JP) .......................... 11-004132

(51) Int. Cl.⁷ .......................... A61K 9/16; A61K 9/14; A61K 38/08
(52) U.S. Cl. .......................... 424/499; 424/489; 514/2; 426/583; 530/330; 530/833
(58) Field of Search .................. 424/489, 499; 530/330, 833; 426/583

(56) References Cited

U.S. PATENT DOCUMENTS 5,449,661 A    9/1995   Nakamura et al.

FOREIGN PATENT DOCUMENTS

| EP | 0 196 813 A1 | 10/1986 |
|----|--------------|---------|
| EP | 0 583 074 A2 | 2/1994 |
| EP | 876816 | * 11/1998 |
| JP | 2782142 | 2/1994 |
| JP | 2782153 | 7/1994 |

OTHER PUBLICATIONS

Sheu, T, Rosenberg M. J. Food Sci., 63(3), 491–494, Mar. 1998.*
Eto et al. J. Jpn.Soc. Nutr. Food Sci., 51, 355–359, Jun. 1988.*
Database CaPlus, DN: 125:141004. Dukalska et al. Latv.Zinat. Acad. Vestis, Sep. 1995, 127–132.*
Databas CaPlus, DN: 128:139981. Ito et al. JP 10033115, Feb. 1998.*
Database CaPlus, DN: 129:160829. Sheu et al. J. Food Sci. (Mar. 1998), 63(3), 491–494.*
Database CaPlus, DN: 129:259540. Velner et al. Proc. Int. Symp. Controlled Release Bioact. Mater. (Feb. 1998), 25th, 300–301.*
Purification and Characterization of Angiotensin I–Converting Enzyme Inhibitors from Sour Milk, *Journal of Dairy Science*, vol. 78, No. 4, 777–782 (1995).

* cited by examiner

*Primary Examiner*—Michael Borin
(74) *Attorney, Agent, or Firm*—Darby & Darby

(57) ABSTRACT

Granules and tablets for oral administration, containing angiotensin-converting enzyme inhibiting peptides and treated whey with a mixing fluid bed processor, wherein said whey is obtained from lactic acid fermentation liquid. The granules have properties of narrow particle distributions, low moisture absorption, and heavy specific gravity, as well as high free flowing. A process is also provided for producing the granules by the steps of:

a) onto seed granules obtained in an earlier operation in a mixing fluid bed processor, spraying purified whey of lactic acid fermentation liquid to form preliminary granules;

b) treating the preliminary granules thus obtained to reduce particle size in a size reduction mill;

c) returning the treated powder to the mixing fluid bed processor, and, d) spraying additional purified whey onto the returned powder in the mixing fluid bed processor to form granules, while fluidizing the said powder.

4 Claims, 1 Drawing Sheet

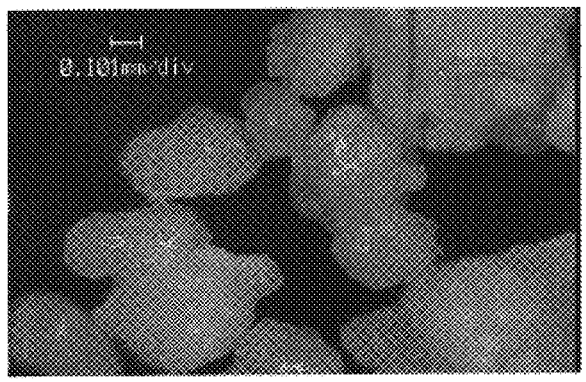
F I G. 1A
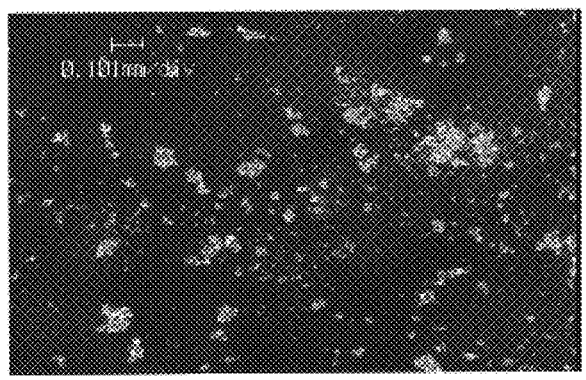
F I G. 1B
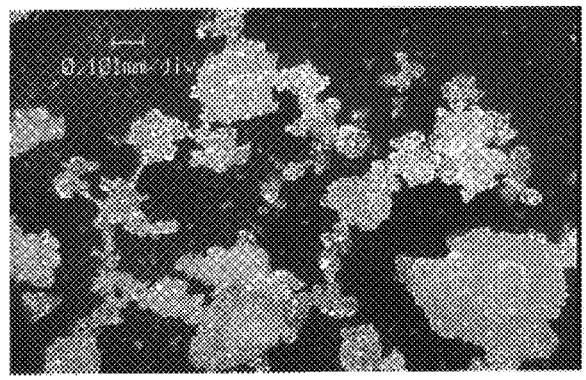
F I G. 1C
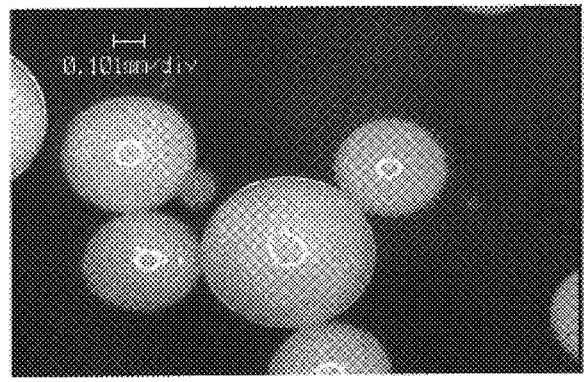
F I G. 1D

PROCESS FOR PRODUCING GRANULES CONTAINING ANGIOTENSIN-CONVERTING ENZYME INHIBITING PEPTIDES

BACKGROUND OF THE INVENTION AND PRIOR ART

The present invention relates to granules for oral administration, containing angiotensin-converting enzyme inhibiting peptides, process for producing the granules, and tablets manufactured from the granules obtained above. The angiotensin-converting enzyme inhibiting peptides are obtained from whey separated from fermentation liquids of lactic acid bacteria or lactic acid bacteria and yeast. The granules and tablets can be used for anti-high blood pressure agent or foods, when the whey is further treated for purification, and then for granulation, and for tableting, if necessary.

The angiotensin-converting enzyme, hereinafter referred to as ACE, is mainly present in lungs and vascular endothelial cells, and acts on angiotensin I (Asp-Arg-Val-Tyr-Ile-His-Pro-Phe-His-Leu) to remove a di-peptide (His-Leu) at its c-terminal and to form angiotensin II, which has a strong blood pressure increasing activity. The ACE also has an ability to decompose and to inactivate bradykinin, which decreases blood pressure. Thus, the ACE acts to increase blood pressure by producing angiotensin II on the one hand, while decomposing bradykinin to increase blood pressure. Accordingly, when the angiotensin-converting enzyme is inhibited, high blood pressure could decrease, and many drugs which contain the angiotensin-converting enzyme inhibitor have been developed and used for anti-high blood pressure.

Certain peptides were recently found to be useful, being low in toxicity and highly safe anti-high blood pressure agents, and natural and synthetic peptides are reported to be probable anti-high blood pressure drugs (Japanese Patent Publication No. 120,225/1991). It is also known that peptides containing Ile-Pro-Pro (hereinafter referred to as IPP) or Val-Pro-Pro (hereinafter referred to as VPP) as its basic peptide structure have ACE inhibiting properties, and that these peptides can be produced in large amounts by culturing certain lactic acid bacteria, or lactic acid bacteria and yeast (Japanese Patents Nos.2,782,142 and 2,782,153). Drugs or foods consisting of the peptides are proposed to be highly safe and useful in a small amount for decreasing high blood pressure in forms of oral administration, when the cultured liquid is treated for purification and separation.

It may be possible to use the fermentation liquid as is obtained in accordance with the processes described in the above patents for the ACE-inhibiting drugs or foods containing the ACE-inhibiting peptides (hereinafter referred to as ACEI peptides). However, these may have poor palatability for oral intake, and are not appropriate to drink without further purification processes, because they contain lactose, lactic acid and some other substances. Accordingly, it is desirable to remove substances other than the ACEI peptides from the liquid. Drugs or foods in a dry form including the peptides in more concentrated form than the liquid are more useful. Proteins and the ACEI peptides having IPP or VPP as its basic peptide structure, which are produced by culturing lactic acid bacteria or lactic acid bacteria and yeast, are partly hydrolyzed to form IPP and VPP in the cultured broths. The IPP and VPP in the peptides mainly show the ACE inhibitory activities.

BRIEF EXPLANATION OF THE INVENTION

The fermentation liquid is subjected to treatments for solid-liquid separation, including centrifugation, decantation, and filtration to obtain whey as a supernatant, which contains a major portion of the ACEI peptides. Acids and other impurities in the whey may be removed by subjecting the whey to one or a combination of the following treatments including electrodialysis, a treatment with ion exchange resins, hollow fiber membrane dialysis, reverse osmosis treatment, and hydrophobic column chromatography.

When the purified whey thus obtained are treated for producing solid oral dosage forms, such as granules, powder, and tablets, by means of conventional drying processes, the products generally have disadvantages, including over-absorption of moisture, lower density, and wider distribution in the particle size, as well as poor free-flowing properties. The wider particle distribution may often decrease efficiency in the following step of tableting, because of its moisture-absorption and poor free-flowing properties.

For example, when the purified solutions are spray-dried, the powder obtained is very fine, and accordingly, moisture absorbant. Its specific gravity is also very small, and particle distribution is very wide. When the purified whey is treated for producing granules by spray-drying and then fluidized bed granulator, the granules obtained have wider particle distribution containing very fine powder, the fine powder should absorb moisture easily, and accordingly, when abruptly exposed to hygroscopic environment, its free-flowing properties greatly decrease. These disadvantages greatly decrease manufacturing efficiency in the next step of tableting operations, for example, the entire environment of the tableting operation should be cooled or under vacuum. Powder which adheres on the surface of the die and punch, causes the tableting machine to stop, and uniform pressures on the surface of the tablets cannot be obtained, because the starting granules cannot smoothly be supplied to the drum with predetermined amounts. Accordingly, the tablets obtained lack uniformity in hardness and gravity. Moreover, manufacturing costs increase, because the procedures necessitate two different equipments and two different operation steps.

Granules obtained by using a spray-drying type fluidized bed granulator have rather narrow distribution in particle size, however, the process for producing the granules has disadvantages, including higher moisture-absorbing properties, and great decrease in the yields of the end product ACEI peptides.

The present invention provides granules for oral administration, containing angiotensin-converting enzyme inhibiting peptides, a process for producing the granules, and tablets manufactured from the granules, wherein the granules and tablets have properties of narrower particle distributions, lower moisture absorption, and heavier specific gravity, as well as higher free-flowing.

The granules manufactured in the present invention are highly safe, effective in ACE inhibitory activities when taken in small amounts, and have good palatability; nevertheless, the whey from which the granules are manufactured contain substances which absorb moisture even in a form of solid dosage forms, too much acids, and other substance.

The present invention also provides manufacturing processes for the granules in high yields of recovering ACEI peptides and ACE inhibitory activities.

BRIEF DESCRIPTION OF THE DRAWINGS

FIG. 1A is a microscopic photograph of granules of the present invention.

FIG. 1B is a microscopic photograph of powder manufactured by spray-drying purified whey.

FIG. 1C is a microscopic photograph of granules manufactured by spray-drying and then fluidized bed granulation from purified whey.

FIG. 1D is a microscopic photograph of granules manufactured by spray-drying type fluidized bed granulator from purified whey.

DETAILED DESCRIPTION OF THE PREFERRED EMBODIMENT

According to the present invention, lactic acid fermentation liquid is subjected to solid-liquid separation, supernatant obtained in which a larger portion of the ACEI peptides are dissolved, and purified by subjecting the supernatant to one or a combination of the following treatments including electrodialysis, a treatment with ion exchange resins, hollow fiber membrane dialysis, reverse osmosis treatment, and hydrophobic column chromatography. Lactic acid, other ions and other substances are removed in great amounts by the treatment, and purified whey thus obtained are used for the starting materials in the present invention to manufacture granules for oral administration containing ACEI peptides.

The purified whey is sprayed onto seed powder, such as lactose and starch which are generally used as seeds, in a mixing fluidized bed processor, while fluidizing, and preliminary granules which contain more than 10% of the seeds, are produced (the first step).

The preliminary granules are non-uniform in particle shape, in which seeds and whey are agglomerated to form coarse lumps, and fine powder having not more than 200 microns almost disappear in the processor (not more than 5%). The preliminary granules are taken out of the processor, and put into a size reduction mill, and the size of the particles are reduced to fine powders having small uniform particles (second step)

The size-reduced fine powder is then returned to the mixing fluid bed processor, and residual purified whey are sprayed onto the fine powder to complete granulation, while fluidizing with hot air under the same conditions as the first step (third step).

The final granules thus obtained are used for the first step of commercial production of the granules; when its size is further reduced, if necessary, commercial operation will repeat the first step, the second step and the third step in turn as described above. The granules of the end product of the invention manufactured by using the above seeds hardly contain foreign seeds as lactose or starch, and accordingly, the granules contain high percentage of the ACEI peptides.

The granules obtained in the present invention have a much narrower distribution of particles than granules and powder obtained by conventional processes. Not less than 70% of the granules generally have bulk density in the range of from 0.6 to 0.8 g/ml and in the range of from 0.1 to 2.0 millimeters particle size can be obtained. Even particles in the range of from 0.2 to 1.0 millimeter and not less than 80% of the granules may also be obtained. This means that the granules are highly free-flowing, and advantageous in the next step of tableting.

The granules also have higher specific density in the range of from 0.6 to 0.8 g/ml, and lower moisture-absorbing property than products manufactured by conventional processes.

Thus, the present invention relates to a process for manufacturing granules for oral administration, containing angiotensin-converting enzyme inhibiting peptides, and having properties of narrow particle distributions, low moisture absorption, and large specific gravity, as well as high free flowing, consisting of the steps of:

a) onto seed granules obtained in an earlier operation in a mixing fluid bed processor, spraying purified whey of lactic acid fermentation liquid to form preliminary granules;

b) treating the preliminary granules thus obtained to reduce particle size in a size-reduction mill;

c) returning the treated powder to the mixing fluid bed processor; and, d) spraying additional purified whey onto the returned powder in the mixing fluid bed processor to form granules, while fluidizing the said powder.

The present invention also relates to granules for oral administration, having such superior properties as narrow particle distributions, low moisture absorption, and large specific gravity, as well as high free flowing.

The granules obtained in the present invention can easily be pressed to compressed tablets of any desired form without the addition of builders. When tableting, 0.5 to 1% emulsifying agent is added and mixed just before starting of the operation as a lubricant. As the granules have high flowability, narrow distribution range in particle size, and low moisture-absorbing properties, tableting pressure is uniformly given to the tablets, and the operation smoothly proceeds without causing any machine trouble and stoppage by such accidents as moistened powder adhering on the surface of the inner vessel, die and punch.

The tablets obtained have very high quality and homogeneity, including hardness, weight per tablet, and size, as well as shape. The surface of the tablets are not necessarily glistening, and have a most suitable and acceptable feel on the tongue, when taken orally.

The procedure for the preparation of the granules and tablets containing angiotensin-converting enzyme inhibiting peptides according to the present invention may be described, by way of explanation, but not limited to, as follows:

EXAMPLE 1

1500 Kg lactic acid fermentation liquid was prepared in accordance with Japanese Patent No.2,782,153, and the liquid was subjected to a solid-liquid separation to obtain 650 kg supernatant. The supernatant was concentrated to 92 kg under vacuum in a long plate type evaporator, "Super-Long plate evaporator RET-100," manufactured by Hisaka Co., Ltd. to a total volume of one seveth (1/7), and a concentrated whey was obtained.

3 Kg each of the concentrated whey was subjected to an electrodialysis for purification by using a unit of TS-2-10 type dialyzer, manufactured by Tokuyama Co., Ltd., Japan, at 15 to 30° C. for 620 minutes with a total current 15.5 AH. 50 Kg of the purified whey containing 37.9 mg VPP and 25.3 mg IPP was obtained by repeating the above treatment.

In the present invention, ACEI activity of IPP is 1.7 times that of VPP, and accordingly, the amount of ACEI peptides is defined and expressed combined amounts of IPP and VPP calculated by the following formula:

Amount of ACEI peptides (mg/100 g)=amount of IPP (mg/100 g)×1.7+amount of VPP (mg/100 g)

The purified whey solutions contained pH3. 0, 0.94% acid, 97.0 units/ml of ACEI activity, and 80.9 mg/100 g ACEI peptides (2.64 mg/100 g solid matter).

300 g lactose (DMV mesh size*200) were thrown into a mixing fluid bed processor "MP-01" model, distributed by Powrex Corporation, Japan, 2177 g purified whey (containing 27.5% solid matter) were sprayed onto the lactose through two fluid nozzles for two hours, fluidizing with hot air blowing, 940 g preliminary granules were obtained.

The operating conditions were as follows:
Inlet air temperature: 80° C.
Outlet air temperature: 50 to 55° C.
Amount of atomized air: 30 liter/second
The blade rotator: 300 r.p.m.

The preliminary granules were subjected to size reduction in a size-reduction mill, "Quadro™ Comil 197" manufactured by Quadro, Inc., U.S.A., so as not to leave particles of size not less than 16 mesh, by using outlet screen holes of 0.8 millimeter diameter.

300 g of the fine powder obtained by the size reduction step above were returned to the mixing fluid bed processor as seed powder for commercial granulation, 1000 g purified whey (27.5% solid matter content) were sprayed onto the seed powder for 2 hours, while fluidizing with hot air blowing, and 460 g end product granules were obtained. The operating conditions were the same as in the above. The granules obtained contained 200 mg/100 g ACEI peptides, and 9.4% moisture, and had 0.7 g/ml specific density.

EXAMPLE 2

4 Kg granules as manufactured in Example 1 were subjected to size reduction with a "Quadro™ Comil 197" to reduce particle size until particles of not less than 16 mesh size disappeared.

4 Kg fine powder obtained above were placed in a mixing fluid bed processor "MP-25" model of Powrex Corporation, Japan, as seed powder, and 21.6 kg purified whey (containing 26.5% solid matter) were sprayed onto the seed powder through two fluid nozzles for 5 hours, while fluidizing with hot air blowing. The operating conditions were as follows:

Inlet air temperature: 80° C.
Outlet air temperature: 50 to 55° C.
Amount of atomized air: 30 liters/second
The blade rotator: 300 r.p.m.

9.1 Kg granules of the end product were obtained.

EXAMPLE 3

4 Kg granules as of the end product as obtained in Example 2 were subjected to size reduction with a "Quadro™ Comil 1971" to reduce particle size with outlet screen holes of 0.8 millimeter diameter for the use of seed powder in the next step. 17.6 Kg purified whey were sprayed onto the 4 kg fine seed powder in a mixing fluid bed processor "MP-25" through 2 fluid nozzles, while fluidizing for 4 hours with hot air blowing under the same conditions as in Example 2, and 8.8 kg granules of the end product were obtained. The granules contained 215 mg/100 g ACEI peptides, 9.0% water, and 0.7 g/ml specific gravity. The granules had the following particle distributions:

TABLE 1

| Particle size | Percentage (%) |
| --- | --- |
| Not less than 1000 μm | 7.4 |
| 1000~550 μm | 49.6 |
| 200~550 μm | 40.8 |
| 150~200 μm | 1.8 |
| 74~150 μm | 0.3 |
| not more than 74 μm | 0.1 |

Comparison Tests 1

Spray dried powder, with a "SD-6.3" model, manufactured by "Niro Ashizawa Atomizer Co., Ltd., Japan, granules with a spray-drying and then granulation with a fluid bed granulator, "Flow Coater FLO" model, manufactured by Oogawara Co., Ltd., Japan, and granules with a spray dry type fluidizing bed granulator, of a model "Aglomaster AGM-SD-01", manufactured by Hosokawa Micron Co., Ltd., Japan, were manufactured by using the purified whey as indicated in Table 2, and the results obtained are shown in Table 2.

TABLE 2

|  | Method A | Method B | Method C | Method D |
|---|---|---|---|---|
| ACEI peptide content (mg/100 g) | | | | |
| whey | 53.8 | 53.8 | 53.8 | 53.8 |
| End product | 202 | 155 | 150 | 180 |
| ACE inhibitory activity (unit/g) | | | | |
| whey | 0.65 | 0.65 | 0.65 | 0.65 |
| end product | 2.4 | 1.9 | 1.8 | 2.2 |

TABLE 2-continued

|  | Method A | Method B | Method C | Method D |
|---|---|---|---|---|
| Moisture content (w/w %) | | | | |
| whey | 73.5 | 73.5 | 73.5 | 73.5 |
| end product | 8.9 | 6.8 | 7.6 | 9.2 |
| Moisture absorption of the end product (%) | 2.0 | 11.2 | 6.4 | 9.5 |
| Specific gravity (g/ml) end product | 0.71 | 0.45 | 0.52 | 0.69 |
| Particle distribution (μm) | | | | |
| Not less than 1000 μm | 7.4 | 0 | 0 | 8 |
| 1000~550 μm | 49.6 | 0 | 0 | 52 |
| 200~550 μm | 40.8 | 0 | 0 | 36 |
| 150~200 μm | 1.8 | 0 | 28 | 3.5 |
| 74~150 μm | 0.3 | 8 | 60 | 0.4 |
| not more than 74 μm | 0.1 | 92 | 12 | 0.1 |

Note:
Method A: present invention
Method B: Spray drying
Method C: Spray drying and then fluidized bed granulation
Method D: Spray dry type fluid bed granulator
Moisture absorption (%): Granules or powder were kept in an environment of 65% relative humidity at 25° C. for 6 hours, and water content was measured.
ACE inhibitory activity: 1 unit is defined as that ACE is inhibited 50%.

EXAMPLE 4

Tablets were manufactured by using 1 kg granules obtained in Example 3 at 20° C. with 0.5% sucrose fatty acid ester, manufactured by Daiichi Seiyaku Co., Ltd., Japan, in a controlled environment of low humidity with a tableting machine CLEC-21K model (Φ20, 1R surface), manufactured by Kikukawa Co., Ltd., Japan. Hammering pressure was 4 metric tons, and die was rotated 10 r.p.m. and 400 tablets were obtained of round shape and 2.5 g per tablet were formed. No adhesion of the granules on the surface of the die and punch was observed, and the tablets formed had good uniformity, and suitable hardness for chewing. The tablets had the following properties:

Weight per tablet: 2.5 g
Thickness 6.87 mm
Hardness: 15.8 kg
Combining: good
Free-flowing: good

What we claim is:

1. A process for manufacturing granules containing angiotensin-converting enzyme inhibiting peptides for oral administration, which comprises the steps of:

a) purifying the supernatant of the solid-liquid separation of a lactic acid fermentation of whey to remove the lactic acid and other impurities to form a purified whey having angiotensin-converting enzyme inhibiting properties;

b) spraying the purified whey of the lactic acid fermentation onto seed granules in a mixing fluid bed processor to form preliminary granules;

c) treating the preliminary granules to reduce their size to form powder;

d) returning the powder obtained in step c) to a mixing fluid bed processor, and, e) spraying additional purified whey onto the returned powder while fluidizing the returned powder in a mixing fluid bed processor to form the granules for oral administration.

2. The process for manufacturing granules as set forth in claim 1, wherein not less than 70 percent of the said granules for oral administration are sized in the range of from 0.1 through 2.0 millimeters, and bulk density is in the range of from 0.6 to 0.8 g/ml.

3. The process for manufacturing granules as set forth in claim 1, wherein not less than 80 percent of the said granules for oral administration are sized in the range of from 0.2 through 1.0 millimeters, and bulk density is in the range of from 0.6 to 0.8 g/ml.

4. The process for manufacturing granules as set forth in claim 1, wherein not less than 70 percent of the said granules for oral administration are sized in the range of from 0.1 through 2.0 millimeters, and bulk density is in the range of from 0.6 to 0.8 g/ml.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Homo sapien

<400> SEQUENCE: 1

Asp Arg Val Tyr Ile His Pro Phe His Leu
1               5                   10